United States Patent
Yakura et al.

(10) Patent No.: US 12,138,105 B2
(45) Date of Patent: Nov. 12, 2024

(54) BIOLOGICAL SOUND MEASUREMENT DEVICE, CONTROL METHOD FOR BIOLOGICAL SOUND MEASUREMENT DEVICE, AND NON-TRANSITORY RECORDING MEDIUM STORING CONTROL PROGRAM FOR BIOLOGICAL SOUND MEASUREMENT DEVICE

(71) Applicant: OMRON HEALTHCARE Co., Ltd., Kyoto (JP)

(72) Inventors: Nobuki Yakura, Kyoto (JP); Katsuyoshi Morita, Kyoto (JP); Keisuke Kimura, Kyoto (JP); Koji Tsukamoto, Kyoto (JP); Tomoki Irago, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 636 days.

(21) Appl. No.: 17/444,317

(22) Filed: Aug. 3, 2021

(65) Prior Publication Data

US 2021/0361255 A1    Nov. 25, 2021

Related U.S. Application Data

(63) Continuation of application No. PCT/JP2020/000753, filed on Jan. 10, 2020.

(30) Foreign Application Priority Data

Feb. 6, 2019  (JP) ................... 2019-020130

(51) Int. Cl.
*A61B 7/00*    (2006.01)
*A61B 5/00*    (2006.01)
(Continued)

(52) U.S. Cl.
CPC ............ *A61B 7/003* (2013.01); *A61B 5/0816* (2013.01); *A61B 5/6843* (2013.01); *A61B 5/72* (2013.01)

(58) Field of Classification Search
CPC ..... A61B 7/003; A61B 5/0816; A61B 5/6843; A61B 5/72; A61B 5/08; A61B 7/005; A61B 7/04; A61B 7/00–045
See application file for complete search history.

(56) References Cited

U.S. PATENT DOCUMENTS

2008/0232604 A1   9/2008  Dufresne et al.
2015/0088021 A1*  3/2015  Tseng ..................... A61B 7/04
                                                    600/528

(Continued)

FOREIGN PATENT DOCUMENTS

CN    109070483 A  * 12/2018  .............. B25J 15/02
JP    2010-522039 A    7/2010

(Continued)

OTHER PUBLICATIONS

English Translation of WO 2015056434 A1, Asahi Kasei Corporation, 30 pages, printed on Mar. 14, 2024,. (Year: 2015).*

(Continued)

*Primary Examiner* — Matthew Kremer
*Assistant Examiner* — Jennifer Grace Baires-Tweed
(74) *Attorney, Agent, or Firm* — Birch, Stewart, Kolasch & Birch, LLP (57) ABSTRACT

Provided are a biological sound measurement device capable of detecting contact with a body surface of a living body with a simple configuration, a control method for the biological sound measurement device, and a non-transitory recording medium storing a control program for the biological sound measurement device. The biological sound measurement device (1) includes: a measuring unit (3) that (Continued)

detects a biological sound of a living body in a state of contact with a body surface S of the living body; and a contact state determination unit (41) that determines whether or not a contact state is active in which the measuring unit (3) is in contact with the body surface S, based on a change in a sound pressure level of sounds detected by the measuring unit (3).

8 Claims, 8 Drawing Sheets

(51) Int. Cl.
*A61B 5/08* (2006.01)
*A61B 7/04* (2006.01)

(56) References Cited

U.S. PATENT DOCUMENTS

2020/0289083 A1    9/2020  Ogawa
2021/0077056 A1*   3/2021  Matsumoto .............. A61B 7/04

FOREIGN PATENT DOCUMENTS

| | | | |
|---|---|---|---|
| JP | 2012-024391 A | 2/2012 | |
| JP | 2015-020030 A | 2/2015 | |
| JP | 2016-158806 A | 9/2016 | |
| JP | 2017-074190 A | 4/2017 | |
| WO | WO-2015012265 A1 * | 1/2015 | ........... A61B 5/6843 |
| WO | WO-2015056434 A1 * | 4/2015 | ......... A61B 5/02416 |
| WO | 2017/042875 A1 | 3/2017 | |
| WO | WO 2017/159752 A1 | 9/2017 | |

OTHER PUBLICATIONS

English Translation of WO 2015012265 A1, Sharp Corporation, 15 pages, printed on Mar. 14, 2024,. (Year: 2015).*
English Translation of CN 109070483 A, Abb Technology AG, 9 pages, printed on Mar. 14, 2024,. (Year: 2018).*
German Office Action for German Application No. 112020000205.5, dated Sep. 22, 2023, with English translation.
International Search Report for International Application No. PCT/JP2020/000753 dated Mar. 5, 2020.
The International Preliminary Report on Patentability for International Application No. PCT/JP2020/000753 dated Oct. 6, 2020.

* cited by examiner

BIOLOGICAL SOUND MEASUREMENT DEVICE, CONTROL METHOD FOR BIOLOGICAL SOUND MEASUREMENT DEVICE, AND NON-TRANSITORY RECORDING MEDIUM STORING CONTROL PROGRAM FOR BIOLOGICAL SOUND MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2020/000753, filed Jan. 10, 2020, which application claims priority to Japan Patent Application No. 2019-020130, filed Feb. 6, 2019, which applications are incorporated herein by reference in their entireties.

TECHNICAL FIELD

The present invention relates to a biological sound measurement device that comes into contact with a body surface of a living body when used and also a control method and a non-transitory recording medium storing a control program for the biological sound measurement device.

BACKGROUND ART

A known device uses a microphone to extract an electrical signal of a biological sound including: respiratory sounds, which are physiological sounds originating from the flow of air in an airway induced by breathing; adventitious sounds, which are abnormal sounds caused by a sickness, such as a wheeze and a pleural friction rub; and heart sounds originating from the cardiovascular system (for example, see Patent Documents 1 to 3).

In Patent Document 1, a respiratory measurement device for detecting respiratory sounds is described, in which whether the measurement device is attached is determined using a light source disposed inside a sound collecting member and a photodetector provided outside the sound collecting member.

In Patent Document 2, a biological sound collecting device is described in which a contact sensor that detects contact of a sound collecting unit on a living body surface is used to determine the contact state of the sound collecting unit in relation to the living body surface.

In Patent Document 3, a technique is described in which an optimal attachment position for a device is determined by comparing a plurality of sounds measured by a single microphone at different locations or comparing a plurality of sounds measured by a plurality of microphones attached at different locations.

CITATION LIST

Patent Literature

Patent Document 1: JP 2017-74190 A
Patent Document 2: JP 2015-20030 A
Patent Document 3: JP 2012-24391 A

SUMMARY OF INVENTION

Technical Problem

In a biological sound measurement device that comes into contact with a body surface of a living body and measures a biological sound, analysis processing of a sound measured by a sound collecting unit is preferably started after an adhered state of the sound collecting unit on the body surface is obtained. Thus, it is necessary to detect whether or not the sound collecting unit is in contact with the body surface. In the devices described in Patent Documents 1 and 2, a dedicated device, such as a photodetector or a contact sensor, is required to determine the contact state with the body surface, making it difficult to reduce the size, reduce the weight, and lower the cost of the device.

In the device described in Patent Document 3, the contact state with the body surface cannot be easily determined because sound is measured from different positions on the body surface and a plurality of microphones are required.

The present invention has been made in view of the above circumstances, and the present invention is directed at providing: a biological sound measurement device capable of detecting contact with a body surface of a living body with a simple configuration; a control method for the biological sound measurement device; and a non-transitory recording medium storing a control program for the biological sound measurement device.

Solution to Problem (1)
A biological sound measurement device, including:
  a sound collecting unit that detects a biological sound of a living body in a state of contact with a body surface of the living body; and
  a contact state determination unit that determines whether or not a contact state is active in which the sound collecting unit is in contact with the body surface, based on a change in a sound pressure level of sounds detected by the sound collecting unit.

According to (1), the contact state is determined on the basis of a change in the sound pressure level of the sounds detected by the sound collecting unit. Accordingly, the contact state can be determined without using a dedicated device, such as a light-emitting unit or a contact sensor, and without detecting biological sounds under different conditions. Thus, the cost, size, and weight of the device can be reduced.

(2)
The biological sound measurement device according to (1) has a configuration wherein
  the contact state determination unit determines the contact state to be active in a case where, after the sound pressure level increases by a value equal to or greater than a first threshold, the sound pressure level decreases by a value equal to or greater than a second threshold and less than the first threshold.

According to (2), the contact state can be determined with high accuracy.

(3)
The biological sound measurement device according to (1) has a configuration wherein
  the contact state determination unit determines the contact state to be active in a case where, after the sound pressure level increases by a value equal to or greater than a first threshold and then the sound pressure level decreases by a value equal to or greater than a second threshold and less than the first threshold, an amount of fluctuation in the sound pressure level is equal to or less than a third threshold continuously for a predetermined amount of time.

According to (3), the contact state can be determined with high accuracy.

(4)

The biological sound measurement device according to (1) has a configuration wherein the contact state determination unit determines the contact state to be active in a case where, after the sound pressure level increases by a value equal to or greater than a first threshold and then the sound pressure level decreases by a value equal to or greater than a second threshold and less than the first threshold, a biological sound is determined to be included in sounds detected by the sound collecting unit.

According to (4), the contact state can be determined with high accuracy.

(5)

The biological sound measurement device according to (1) has a configuration wherein the contact state determination unit determines whether or not a contact state is active in which the sound collecting unit is in contact with the body surface, based on a change in a sound pressure level of a specific frequency band of sounds detected by the sound collecting unit.

According to (5), the contact state can be determined with high accuracy.

(6)

The biological sound measurement device according to (5), wherein the specific frequency band is a frequency band of 100 Hz and below.

According to (6), the contact state can be determined with high accuracy.

(7)

The biological sound measurement device according to any one of (1) to (6) further includes a control unit that analyzes sounds detected by the sound collecting unit and notifies of an analysis result, wherein the control unit starts analysis of the sounds in a case where the contact state determination unit determines that the contact state is active.

According to (7), the sound analysis is started simply by the measurer bringing the sound collecting unit into contact with the body surface of the living body. As a result, analysis of biological sounds can start simply, smoothly, and intuitively.

(8)

The biological sound measurement device according to (7) has a configuration wherein the control unit analyzes the sounds and notifies of an analysis result indicating whether or not a wheeze is included in the sounds.

According to (8), because the measurer is notified of the presence or absence of a wheeze, a treatment strategy for the subject can be planned.

(9)

A control method for a biological sound measurement device includes: determining whether or not a contact state is active in which a sound collecting unit of a biological sound measurement device, the sound collecting unit detecting a biological sound of a living body in a state of contact with a body surface of the living body, is in contact with the body surface, based on a change in a sound pressure level of sounds detected by the sound collecting unit.

According to (9), the contact state is determined on the basis of a change in the sound pressure level of the sounds detected by the sound collecting unit. Accordingly, the contact state can be determined without using a dedicated device, such as a light-emitting unit or a contact sensor, and without detecting biological sounds under different conditions. Thus, the cost, size, and weight of the device can be reduced.

(10)

A control program for a biological sound measurement device for causing a computer to execute:

determining whether or not a contact state is active in which a sound collecting unit of a biological sound measurement device, the sound collecting unit detecting a biological sound of a living body in a state of contact with a body surface of the living body, is in contact with the body surface, based on a change in a sound pressure level of sounds detected by the sound collecting unit.

According to (10), the contact state is determined on the basis of a change in the sound pressure level of the sounds detected by the sound collecting unit. Accordingly, the contact state can be determined without using a dedicated device, such as a light-emitting unit or a contact sensor, and without detecting biological sounds under different conditions. Thus, the cost, size, and weight of the device can be reduced.

Advantageous Effects of Invention

The present invention can provide: a biological sound measurement device capable of detecting contact with a body surface of a living body with a simple configuration; a control method for the biological sound measurement device; and a non-transitory recording medium storing a control program for the biological sound measurement device.

DESCRIPTION OF EMBODIMENTS

Overview of a Biological Sound Measurement Device According to an Embodiment

An overview of a biological sound measurement device according to an embodiment of the present invention will now be described. The biological sound measurement device of an embodiment, via a measuring unit, the measuring unit configured to be placed on an area between the ribs of a person, measures pulmonary sounds (respiratory sounds and adventitious sounds) as an example of a biological sound. In a case where a wheeze is determined to be included as an adventitious sound in the measured sound, the biological sound measurement device issues a notification of this. In this manner, it supports determination of whether or not medication needs to be given to a subject, whether or not a subject should be taken to the hospital, and the diagnosis of a subject by a physician.

The biological sound measurement device of an embodiment includes the measuring unit including a housing that houses a sound detecting element for detecting pulmonary sounds. The biological sound measurement device detects pulmonary sounds of a living body by sealing, with a body surface, the space inside the housing where the sound detecting element is housed and, in this state, by detecting pressure fluctuations in the space by the sound detecting element.

The biological sound measurement device of an embodiment monitors a sound pressure level of the sound detected by the sound detecting element and determines whether or not the measuring unit is in a contact state with the body surface of the living body on the basis of the changes in the sound pressure level. As described above, because the contact state is determined on the basis of the sound pressure level of the sound detected by the sound detecting element used to detect pulmonary sounds, a dedicated device for determining the contact state and detection of sounds under different conditions are unnecessary. Thus, the cost, size, and weight of the device can be reduced. A specific example of the configuration of a biological sound measurement device according to an embodiment will be described below.

Embodiment

Figure 1:
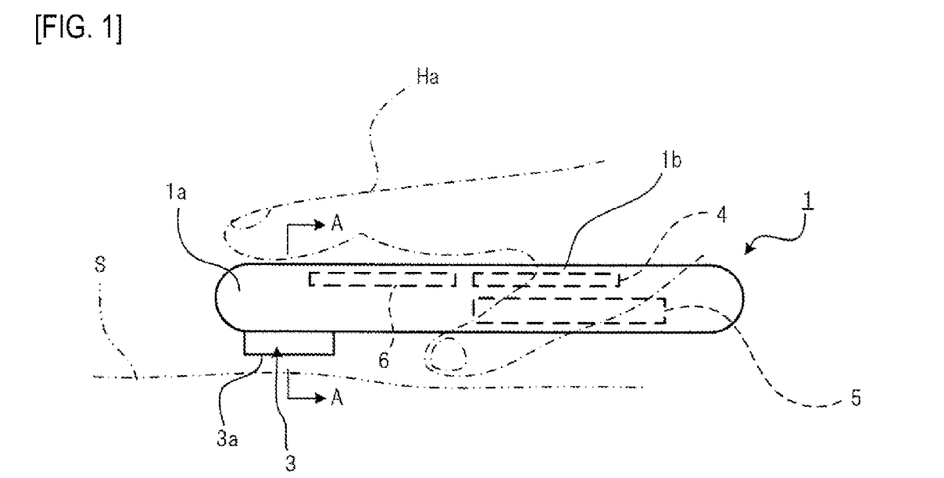
FIG. 1 is a side view illustrating a schematic example configuration of a biological sound measurement device 1, which is an embodiment of the biological sound measurement device of the present invention.

FIG. 1 is a side view illustrating a schematic example configuration of a biological sound measurement device 1, which is an embodiment of the biological sound measurement device of the present invention. As illustrated in FIG. 1, the biological sound measurement device 1 includes: a body portion 1b, which is a case made of resin or metal; and a head portion 1a provided on a first end side of the body portion 1b.

The body portion 1b is provided with: a control unit 4 that executes overall control, a battery 5 that supplies the necessary voltage for operation, and a display unit 6 that displays images via a liquid crystal display panel, an organic electro luminescence (EL) display panel, or the like.

The control unit 4 includes a central processing unit (CPU), random-access memory (RAM), read-only memory (ROM), and the like, and controls each hardware component of the biological sound measurement device 1 according to a program. The ROM of the control unit 4 stores a program including a control program for the biological sound measurement device 1.

The head portion 1a is provided with a measuring unit 3 that projects toward a first side (downward in FIG. 1) in a direction roughly orthogonal to the longitudinal direction of the biological sound measurement device 1. The leading end of the measuring unit 3 is provided with a pressure receiving unit 3a that is brought into contact with a body surface S of a living body, i.e., a subject, and receives pressure from the body surface S.

The biological sound measurement device 1 is used by the pressure receiving unit 3a of the measuring unit 3 being pressed by the index finger of a user's hand Ha against the body surface S, with the index finger being placed on the back surface of the measuring unit 3 at the head portion 1a.

Figure 2:
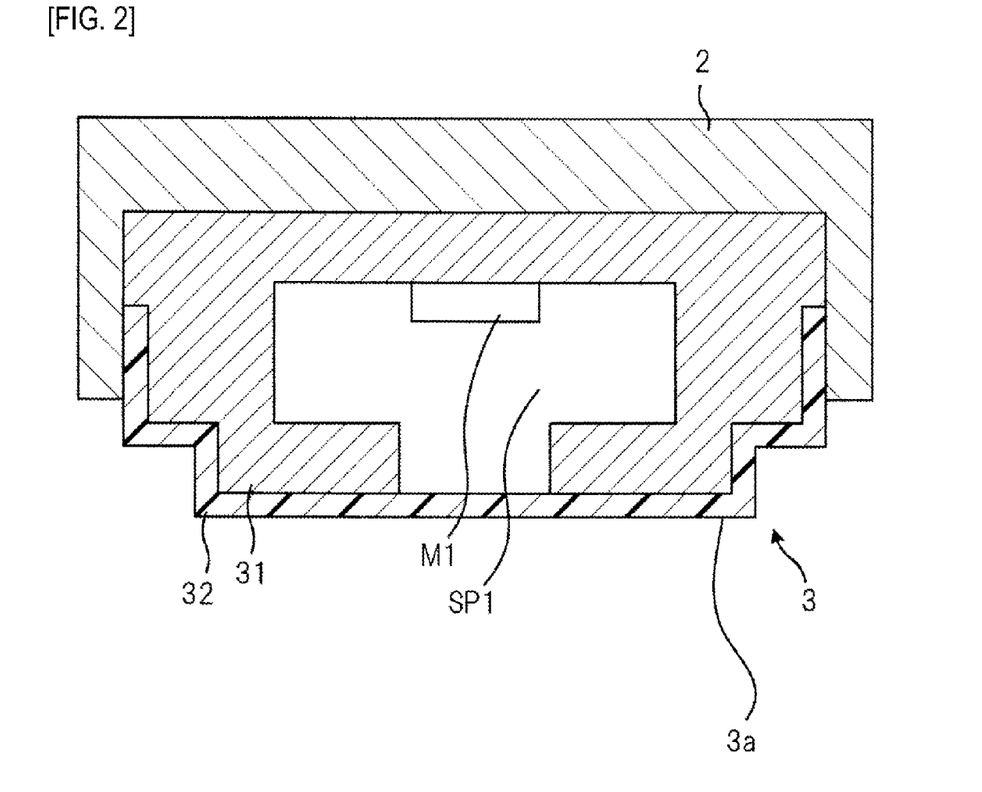
FIG. 2 is a schematic cross-sectional view along line A-A of the biological sound measurement device 1 illustrated in FIG. 1.

FIG. 2 is a schematic cross-sectional view along line A-A of the biological sound measurement device 1 illustrated in FIG. 1. The measuring unit 3 is provided with: a housing 31 with a closed bottom, which is a member that forms a housing space SP1 that is sealed by the body surface S when pressed; a sound detecting element M1 that detects sound disposed in the housing space SP1 of the housing 31; and a housing cover 32 that closes the housing space SP1 from the outside and covers the housing 31.

The measuring unit 3 is engaged with an opening portion formed on a case 2 forming the head portion 1a and is fixed to the case 2, with a portion of the housing cover 32 exposed.

The leading end portion of the housing cover 32 of the portion exposed from the case 2 is shaped as a flat surface or a curved surface, with this flat surface or curved surface forming the pressure receiving unit 3a illustrated in FIG. 1.

The external shape of the housing 31 is roughly a protrusion-like shape pointed downward in FIG. 2. The housing 31 is made of a material, such as a resin or metal, having higher acoustic impedance than air and having high rigidity. The housing 31 is preferably made of a material that reflects sound in a measurement frequency band of the sound detecting element M1, making it difficult for sound from the outside to transmit inside the housing space SP1 when the housing 31 is in contact with the body surface S.

The housing cover 32 is a cylindrical member with a closed bottom, and the shape of the hollow portion of the housing cover 32 is substantially the same as the outer wall shape of the housing 31.

The housing cover 32 is made of a material with an acoustic impedance that is close to that of the human body, air, or water and having good flexibility and good biocompatibility. Examples of the material of the housing cover 32 include silicone, an elastomer, and the like.

The sound detecting element M1 is configured to detect pulmonary sounds, i.e., the measurement target of the biological sound measurement device 1 and is composed of, for example, a micro electro-mechanical systems (MEMS) microphone or a capacitance-type microphone that detects sounds in a band (for example, a frequency range ranging from 1 Hz to 10 kHz) wider than the frequency range (typically, a range from 10 Hz to 1.5 kHz) of pulmonary sounds.

The sound detecting element M1 is electrically connected to the control unit 4 illustrated in FIG. 1 by a lead wire, which is not illustrated, and transmits the detected sound information to the control unit 4.

To use the biological sound measurement device 1, the pressure receiving unit 3a of the housing cover 32 is brought into contact with the body surface S, and, under pressure from the body surface S, the housing space SP1 is sealed by the body surface S via the housing cover 32. Then, when the pressure receiving unit 3a vibrates due to the pulmonary sounds transmitted from the living body to the body surface S, the internal pressure of the housing space SP1 fluctuates due to this vibration, and by this fluctuation in the internal pressure, an electrical signal corresponding to the pulmonary sound is detected by the sound detecting element M1. The measuring unit 3 forms a sound collecting unit for detecting biological sounds when in contact with the body surface S.

Figure 3:
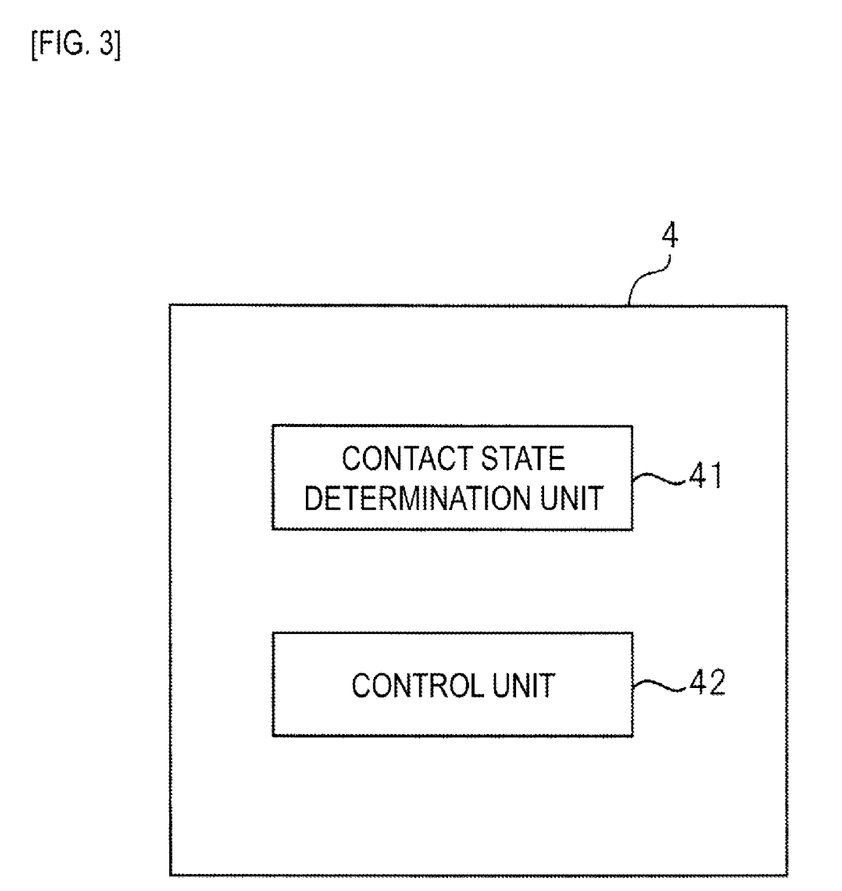
FIG. 3 is a diagram illustrating functional blocks of a control unit 4 of the biological sound measurement device 1 illustrated in FIG. 1.

FIG. 3 is a diagram illustrating functional blocks of the control unit 4 of the biological sound measurement device 1 illustrated in FIG. 1. The processor of the control unit 4 functions as a contact state determination unit 41 and a control unit 42 by executing the control program described above stored in the ROM.

The contact state determination unit 41 determines whether or not the measuring unit 3 is in contact with the body surface S on the basis of the sound pressure level of the sound detected by the sound detecting element M1.

Figure 4:
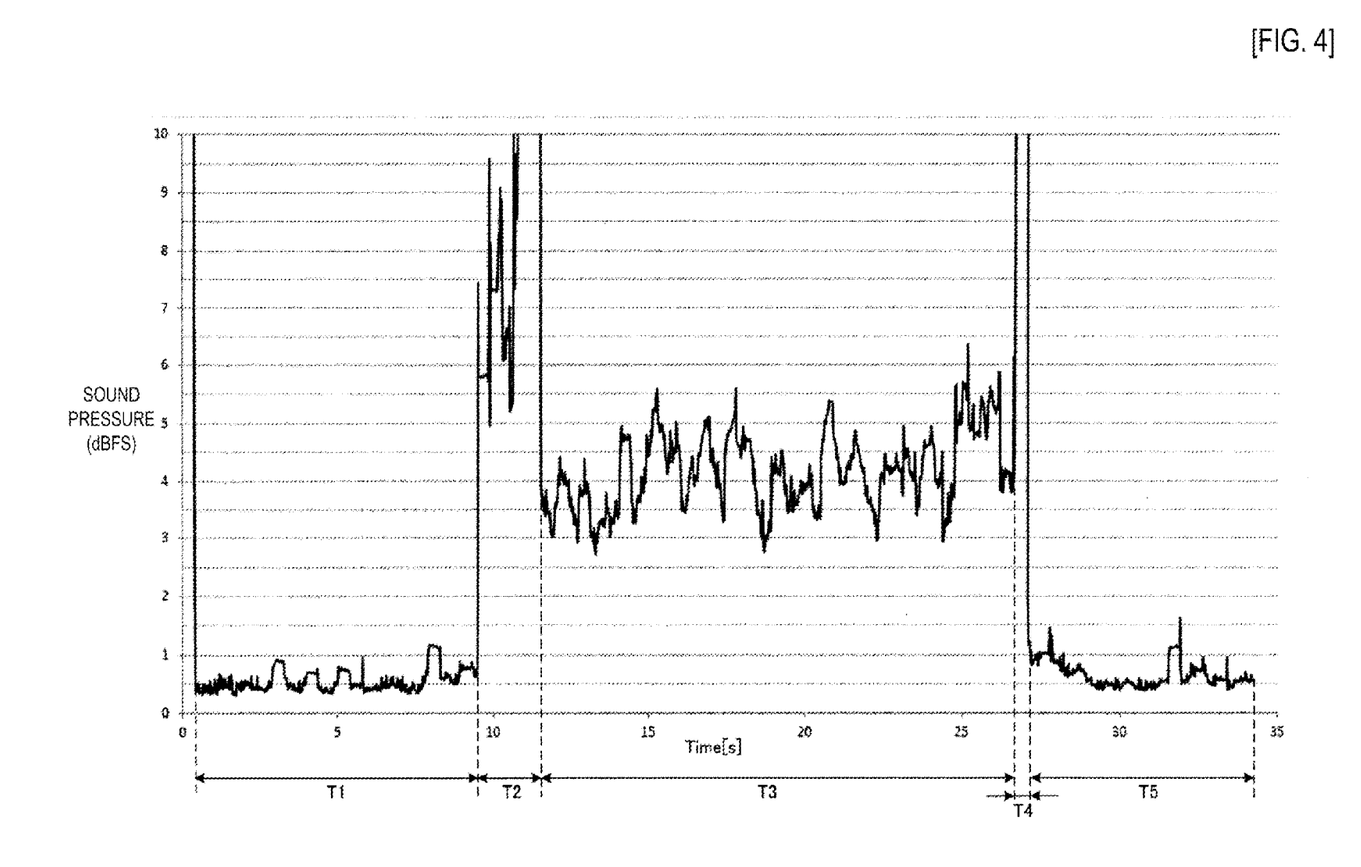
FIG. 4 is a diagram showing an example of changes in the sound pressure level of the sound detected by a sound detecting element M1 of the biological sound measurement device 1.

FIG. 4 is a diagram showing an example of changes in the sound pressure level of the sound detected by the sound detecting element M1 of the biological sound measurement device 1. Shown in FIG. 4 are the changes in the sound pressure level obtained when the pressure receiving unit 3a of the measuring unit 3 comes into contact with the body surface S from a state of non-contact with the body surface S, the pressure receiving unit 3a is held in that state for a while, and then the pressure receiving unit 3a is separated from the body surface S and put in a non-contact state.

A time period T1 shown in FIG. 4 indicates a time period in which the pressure receiving unit 3a of the measuring unit 3 is not in contact with the body surface S. A time period T2 shown in FIG. 4 indicates a time period directly after when the pressure receiving unit 3a of the measuring unit 3 is brought in contact with the body surface S. A time period T3 shown in FIG. 4 indicates a time period in which the pressure receiving unit 3a of the measuring unit 3 is in contact with the body surface S and held in this state. A time period T4 shown in FIG. 4 indicates a time period directly after when the pressure receiving unit 3a of the measuring unit 3 is separated from the body surface S and put into a non-contact state. A time period T5 shown in FIG. 4 indicates a time period after a short amount of time has passed since the pressure receiving unit 3a of the measuring unit 3 was put in a non-contact state with the body surface S.

As shown in FIG. 4, in the time period T1 and the time period T5 in which the pressure receiving unit 3a is not in contact with the body surface S, the sound pressure level of the sound detected by the sound detecting element M1 moves to a low value. This is because, when the pressure receiving unit 3a is not in contact with an object, the vibration of the pressure receiving unit 3a does not increase unless a large sound is produced near the biological sound measurement device 1.

When there is a transition from a state in which the pressure receiving unit 3a is not in contact with the body surface S to a state in which the pressure receiving unit 3a is in contact with the body surface S, directly after this transition, the vibrations of the pressure receiving unit 3a increase due to the pressure receiving unit 3a and the body surface S coming into contact. Thus, as shown in FIG. 4, at the time period T2, the sound pressure levels temporarily reach high values. After a short time has passed since contact between the pressure receiving unit 3a and the body surface S, the pressure receiving unit 3a mainly vibrates due to the biological sounds transmitted to the body surface S. Thus, as shown in FIG. 4, in the time period T3 after a short time has passed since contact between the pressure receiving unit 3a and the body surface S, the sound pressure levels are less than those in the time period T2. Here, the sound pressure level during the time period T3 has values greater than the sound pressure level during the time period T1 because the pressure receiving unit 3a is caused to vibrate by the biological sounds.

When there is a transition from a state in which the pressure receiving unit 3a is in contact with the body surface S and held thereon to a state in which the pressure receiving unit 3a is separated from the body surface S, directly after this transition, the vibrations of the pressure receiving unit 3a increase due to the pressure receiving unit 3a and the body surface S separating. Thus, as shown in FIG. 4, at the time period T4, the sound pressure levels temporarily reach high values. Then, when a short time passes since separation of the pressure receiving unit 3a and the body surface S, the sound pressure level transitions to a level similar to the values in the time period T1.

Accordingly, it can be seen that when the pressure receiving unit 3a of the measuring unit 3 is brought into contact with the body surface S, from a non-contact state with the body surface S, and held in this state, the sound pressure level of the sounds detected by the sound detecting element M1 temporarily rises, after which it falls and stabilizes at a level higher than the sound pressure level during the non-contact state. Thus, whether or not there is a contact state can be determined by determining whether or not such changes are present in the sound pressure levels.

Specifically, when sound detection by the sound detecting element M1 is started and storage of the sound pressure level information to the RAM is started, the contact state determination unit 41 obtains, from the RAM, the sound pressure level information for each unit processing period (for example, a few ms or a few tens of ms) from the sound detection starting time and calculates the average value of the obtained sound pressure levels. The contact state determination unit 41 sequentially advances from the starting time of the unit processing period by an amount of time shorter than the unit processing period, for example, and sequentially calculates the average value of the sound pressure levels of each unit processing period.

The contact state determination unit 41 compares a first average value calculated for a freely selected unit processing period with a second average value calculated for a unit processing period after the unit processing period has advanced by one and, in a case where the second average value is greater than the first average value by a value equal to or greater than a predetermined first threshold, determines that a transition from a non-contact state to a contact state has occurred. In a case where the second average value is not greater than the first average value by a value equal to or greater than the first threshold, the contact state determination unit 41 determines that a non-contact state is active in which the measuring unit 3 is not in contact with the body surface S.

The first threshold is empirically determined as a minimum value of a value obtained by calculating the difference between the average value of the sound pressure level in the time period T1 and the average value of the sound pressure level in the time period T2 shown in FIG. 4, for example. Also, the first threshold is set to a value sufficiently greater than a value obtained by calculating the difference between the average value of the sound pressure level in the time period T3 and the average value of the sound pressure level in the time period T4 shown in FIG. 4.

Even after the contact state determination unit 41 has determined that a transition from a non-contact state to a contact state, comparison is repeated of the second average value of the sound pressure levels in the latest unit processing period having the latest starting time with the first average value of the sound pressure levels in the unit processing period one before the latest unit processing period. Then, in a case where the second average value is less than the first average value by a value equal to or greater than a second threshold but less than the first threshold, the contact state determination unit 41 determines that a contact state is active in which the measuring unit 3 has come into contact with the body surface S. Note that in a case where the second average value is less than the first average value by a value equal to or greater than the first threshold, the contact state determination unit 41 determines that a transition to a contact state is over and a non-contact state has returned.

The second threshold is empirically determined as a value obtained by subtracting, from the first threshold, a maximum value of a value obtained by calculating the difference between the average value of the sound pressure level in the time period T3 and the average value of the sound pressure level in the time period T1 shown in FIG. 4.

The control unit 42 executes analysis processing to analyze the sounds detected by the sound detecting element M1 and notification processing to issue a notification of the result of the analysis processing (analysis result). The analysis processing is, for example, for: processing the sounds detected by the sound detecting element M1 and determining whether or not an abnormal sound such as a wheeze is included in the sounds. The notification processing is, for example, processing including: notifying of the analysis result by displaying the presence or absence of a wheeze on the display unit 6, notifying of the presence or absence of a wheeze by lighting up a light-emitting element, which is not illustrated, and the like.

In a case where the contact state determination unit 41 determines that the measuring unit 3 is in a contact state, the control unit 42 starts the analysis processing described above.

Operational Example of Biological Sound Measurement Device 1

Figure 5:
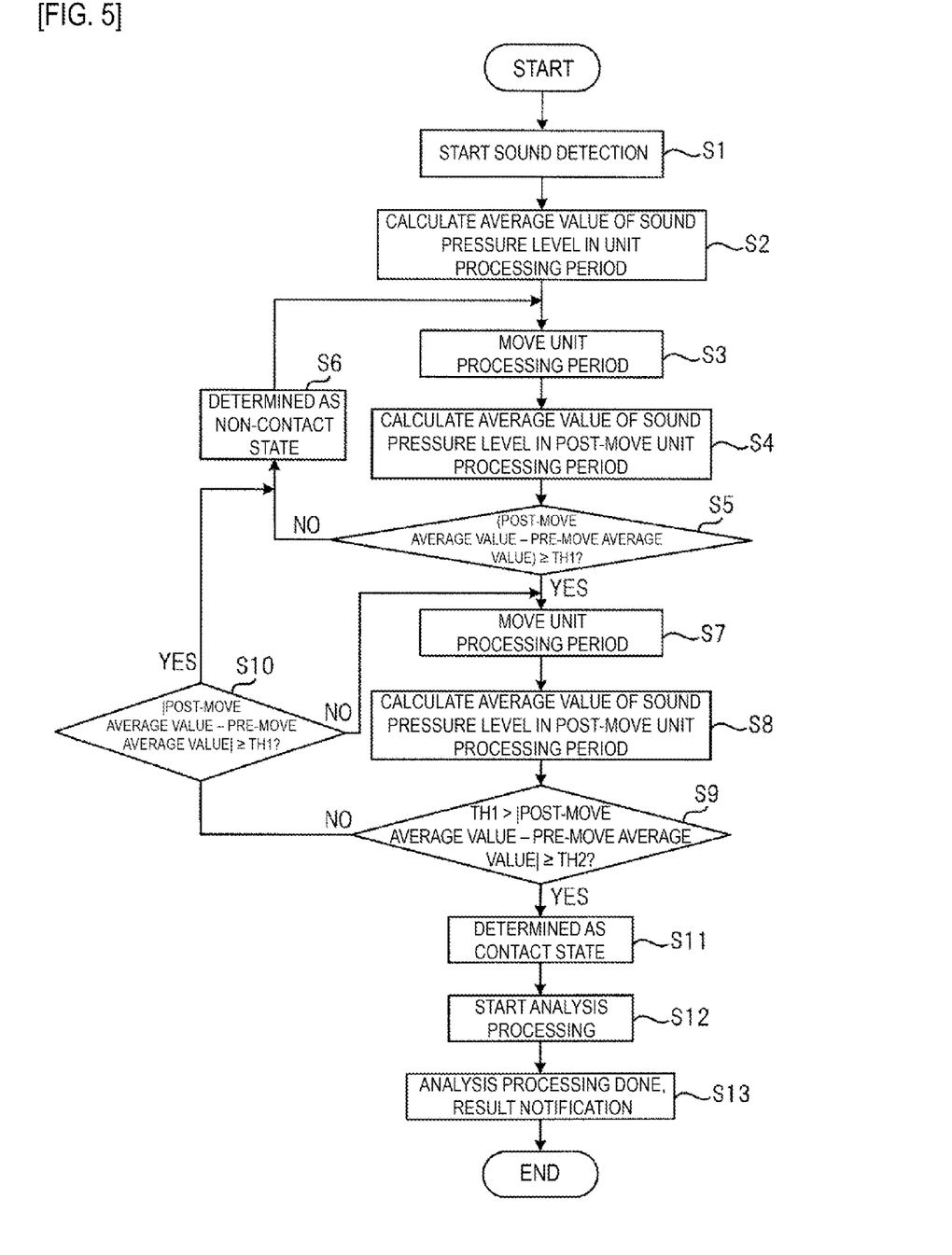
FIG. 5 is a flowchart for describing an operational example of the biological sound measurement device 1 illustrated in FIG. 1.

FIG. 5 is a flowchart for describing an operational example of the biological sound measurement device 1 illustrated in FIG. 1. When the device is powered on, sound detection by the sound detecting element M1 is started, and the detected sounds information (including the sound pressure level) and the sound detection time information are stored in the RAM (step S1).

When the sound information for a certain time period is stored in the RAM, the contact state determination unit 41 obtains the sound pressure levels of the sounds detected in the unit processing period in the information and calculates the average value of the obtained sound pressure level (step S2). Note that, in the initial setting, the unit processing period is set so that the starting time of the unit processing period matches the starting time of the sound information stored in the RAM.

Next, the contact state determination unit 41 advances the starting time of the unit processing period (moves the unit processing period) and re-sets the unit processing period (step S3). Then, the contact state determination unit 41 obtains what is detected in the set unit processing period and calculates the average value of the sound pressure levels obtained, from the sound pressure levels stored in the RAM (step S4).

Next, the contact state determination unit 41 determines whether or not the value obtained by subtracting, from the average value (post-move average value) of the sound pressure levels corresponding to the latest set unit processing period calculated in step S4, the average value (pre-move average value) of the sound pressure levels corresponding to the unit processing period set directly before the latest setting, is equal to or greater than a first threshold TH1 (step S5).

In a case where the determination of step S5 is NO, the contact state determination unit 41 determines that a non-contact state is active in which the measuring unit 3 is not in contact with the body surface S (step S6), and the process moves to step S3.

In a case where the determination of step S5 is YES, the contact state determination unit 41 advances the starting time of the unit processing period (moves the unit processing period) and re-sets the unit processing period (step S7). Then, the contact state determination unit 41 obtains what is detected in the set unit processing period and calculates the average value of the sound pressure levels obtained, from the sound pressure levels stored in the RAM (step S8).

Next, the contact state determination unit 41 determines whether or not a difference (absolute value without a sign), between the average value (post-move average value) of the sound pressure levels corresponding to the latest set unit processing period calculated in step S8 and the average value (pre-move average value) of the sound pressure levels corresponding to the unit processing period set directly before the latest setting, is equal to or greater than a second threshold TH2 and less than the first threshold TH1 (step S9).

In a case where the determination of step S9 is NO, the contact state determination unit 41 determines whether or not the difference described above is equal to or greater than the first threshold TH1 (step S10). In a case where the difference described above is equal to or greater than the first threshold TH1 (YES in step S10), the contact state determination unit 41 moves the process to step S6, and in a case where the difference described above is less than the first threshold TH1 (NO in step S10), the contact state determination unit 41 moves the process to step S7.

In a case where the determination of step S9 is YES, the contact state determination unit 41 determines that a contact state appropriate for biological sound measurement is active in which the measuring unit 3 is contact with the body surface S (step S11).

After step S11, the control unit 42 starts the analysis processing on the sounds detected by the sound detecting element M1 (step S12), and when the analysis processing is complete, the control unit 42 issues a notification of the analysis result (step S13) and the process ends.

Effect of Biological Sound Measurement Device 1

As described above, the biological sound measurement device 1 determines whether or not there is a contact state on the basis of a change in the sound pressure level of the sounds detected by the sound detecting element M1. Accordingly, the contact state can be determined with a simple configuration without using a dedicated device, such as a light-emitting unit or a contact sensor, and without detecting sounds under different conditions. Thus, the cost, size, and weight of the device can be reduced.

In addition, according to the biological sound measurement device 1, a contact state is determined to be active in a case where, after the sound pressure level increases by a value equal to or greater than the first threshold TH1, the sound pressure level decreases by a value equal to or greater than the second threshold TH2 but less than the first threshold TH1, the second threshold TH2 being less than the first threshold TH1. By determining that a contact state is active in a case where, after the sound pressure level greatly increases, the sound pressure level decreases to a level higher than the sound pressure level before the increase, a distinction can be accurately made between the case of a transition from the time period T3 to the time period T5 and the case of a transition from the time period T1 to the time period T3 shown in FIG. 4. Accordingly, whether or not there is a contact state can be determined with high accuracy.

In addition, according to the biological sound measurement device 1, in a case where a contact state is determined to be active, analysis processing of sounds is started. According to this configuration, the measurer can know whether there is a wheeze by simply pressing the measuring unit 3 against the body surface S of the subject, and no special operation after the device is powered on is necessary. In this manner, the convenience of the device is improved. Furthermore, because a user interface such as a button for issuing an instruction to start analysis processing is not necessary, the design of the device can be improved, and the cost of the device can be reduced. The biological sound measurement device 1 is used by the body portion 1b being gripped with one hand and the index finger being placed on the back surface of the measuring unit 3. Thus, being able to start the analysis processing by simply bringing the measuring unit 3 into contact with the body surface S is effective in stabilizing the contact state with the body surface S.

First Modified Example of Biological Sound Measurement Device 1

After YES is determined in step S9 of FIG. 5, the contact state determination unit 41 may determine that a contact state is active in a case where there is little fluctuation in the sound pressure levels continuously for a predetermined amount of time.

Figure 6:
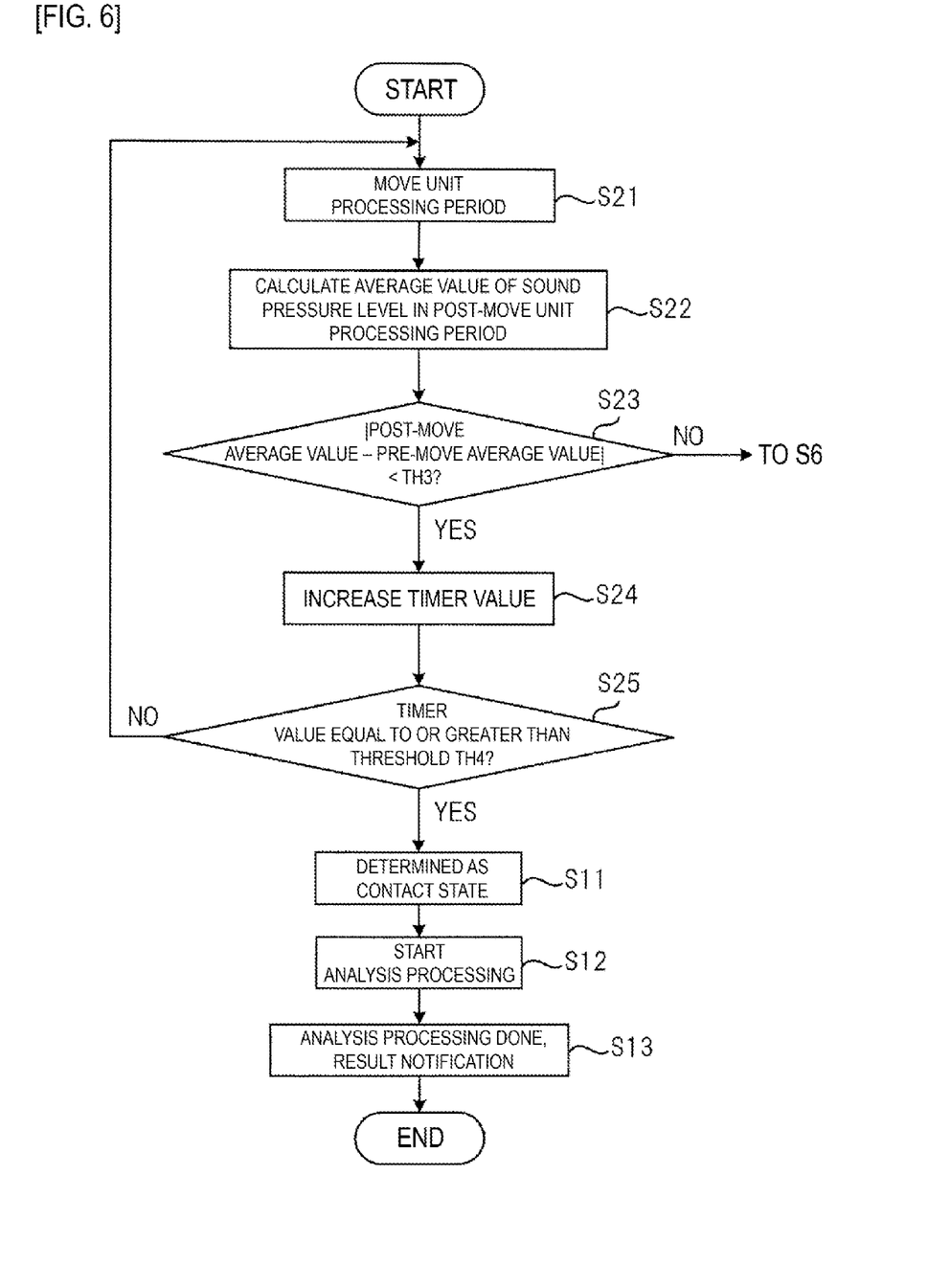
FIG. 6 is a flowchart for describing a modified example of operations executed after YES is determined in step S9 of the flowchart of FIG. 5.

FIG. 6 is a flowchart for describing a modified example of operations executed after YES is determined in step S9 of the flowchart of FIG. 5. In FIG. 6, the same reference signs are used for the same processing as in FIG. 5.

In a case where the determination of step S9 is YES, the contact state determination unit 41 advances the starting time of the unit processing period (moves the unit processing period) and re-sets the unit processing period (step S21). Then, the contact state determination unit 41 obtains what is detected in the set unit processing period and calculates the average value of the sound pressure levels obtained, from the sound pressure level stored in the RAM (step S22).

Next, the contact state determination unit 41 determines whether or not a difference (absolute value without a sign), between the average value (post-move average value) of the sound pressure levels corresponding to the latest set unit processing period calculated in step S22 and the average value (pre-move average value) of the sound pressure levels corresponding to the unit processing period set directly before the latest setting, is less than a third threshold TH3 (step S23). The third threshold TH3 is set to determine whether or not the measuring unit 3 is held in contact with the body surface S and is a value sufficiently less than the first threshold TH1 and the second threshold TH2.

In a case where the determination of step S23 is NO, the contact state determination unit 41 moves the process to step S6, and in a case where the determination of step S23 is YES, the contact state determination unit 41 increases a timer value by one (step S24). Note that the initial value of the timer value is 0.

After step S24, the contact state determination unit 41 determines whether or not the timer value is equal to or greater than a threshold TH4 (step S25). In a case where the timer value is less than the threshold TH4 (NO in step S25), the contact state determination unit 41 returns the process to step S21.

In a case where the timer value is equal to or greater than the threshold TH4 (YES in step S25), the contact state determination unit 41 moves the process to step S11.

As described above, in the first modified example, a contact state is determined to be active in a case where, after the sound pressure level greatly increases, the sound pressure level decreases to a level higher than the sound pressure level before the increase, and the amount of fluctuation in the sound pressure level after this movement is equal to or less than the third threshold TH3 for a certain continuous amount of time. There are cases where after the measuring unit 3 is brought in contact with the body surface S, the measuring unit 3 is then quickly separated from the body surface S. According to the first modified example, because such cases do not result in a contact state determination, the accuracy of determining whether or not a contact state is active can be increased.

Second Modified Example of Biological Sound Measurement Device 1

After YES is determined in step S9 of FIG. 5, the contact state determination unit 41 may determine that a contact state is active in a case where a biological sound is determined to be included in the sounds detected by the sound detecting element M1.

Figure 7:
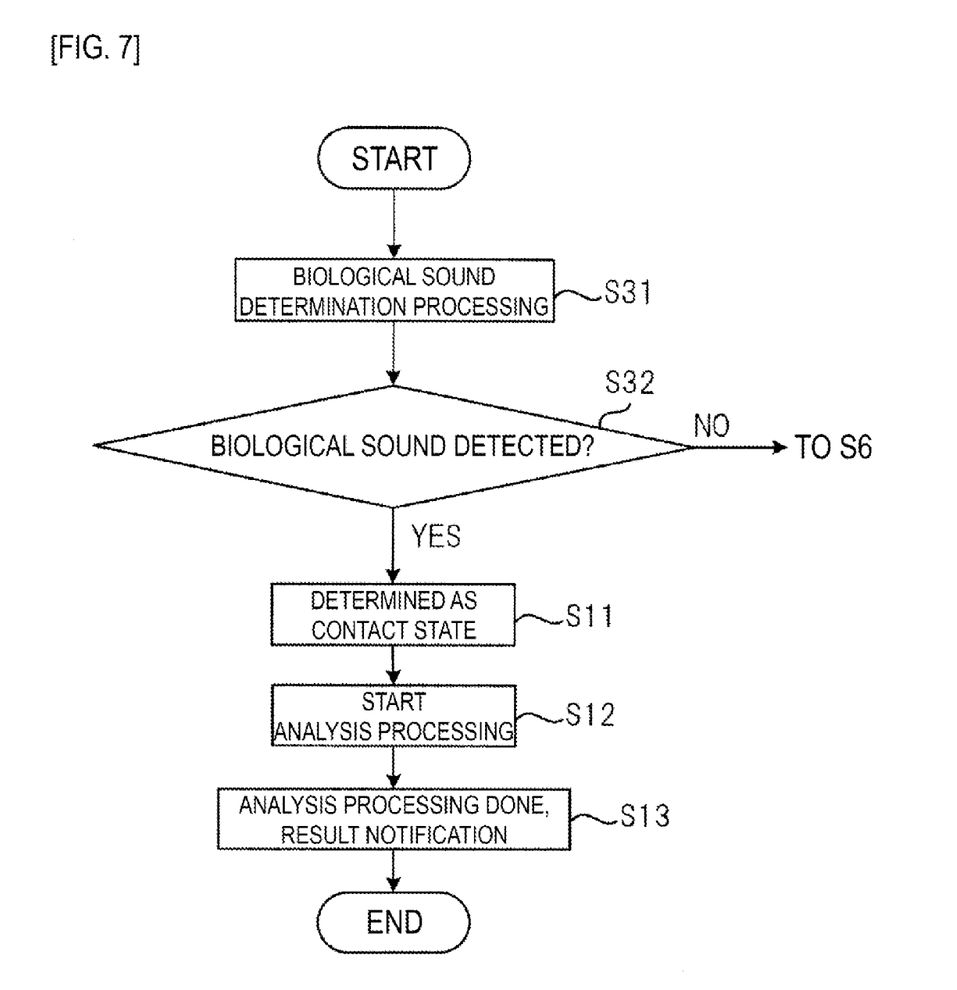
FIG. 7 is a flowchart for describing a modified example of operations executed after YES is determined in step S9 of the flowchart of FIG. 5.

FIG. 7 is a flowchart for describing a modified example of operations executed after YES is determined in step S9 of the flowchart of FIG. 5. In FIG. 7, the same reference signs are used for the same processing as in FIG. 5.

After YES is determined in step S9, the contact state determination unit 41 may execute biological sound determination processing to determine whether or not a biological sound is included in the sounds detected by the sound detecting element M1 (step S31). For example, the contact state determination unit 41 executes frequency analysis on the sounds detected by the sound detecting element M1. The contact state determination unit 41 determines that a biological sound is detected, in a case where the sounds include a frequency band in which a biological sound can be found, and determines that no biological sounds are detected, in a case where the sounds do not include a frequency band in which a biological sound can be found.

In a case where the result of the determination processing of step S31 is that no biological sound is detected (NO in step S32), the process moves to step S6. In a case where a biological sound is detected (YES in step S32), the processing of step S11 onward is executed.

As described above, in the second modified example, a contact state is determined to be active in a case where, after the sound pressure level greatly increases, the sound pressure level decreases to a level higher than the sound pressure level before the increase, and a biological sound is determined to be included in the sounds detected after this movement. There are cases where after the measuring unit 3 is brought in contact with the body surface S, the measuring unit 3 is then quickly separated from the body surface S. According to the second modified example, because such cases do not result in a contact state determination, the accuracy of determining whether or not a contact state is active can be increased.

Third Modified Example of Biological Sound Measurement Device 1

The contact state determination unit 41 may determine whether or not a contact state is active on the basis of a change in the sound pressure level of a specific frequency band from among the sounds detected by the sound detecting element M1.

Figure 8:
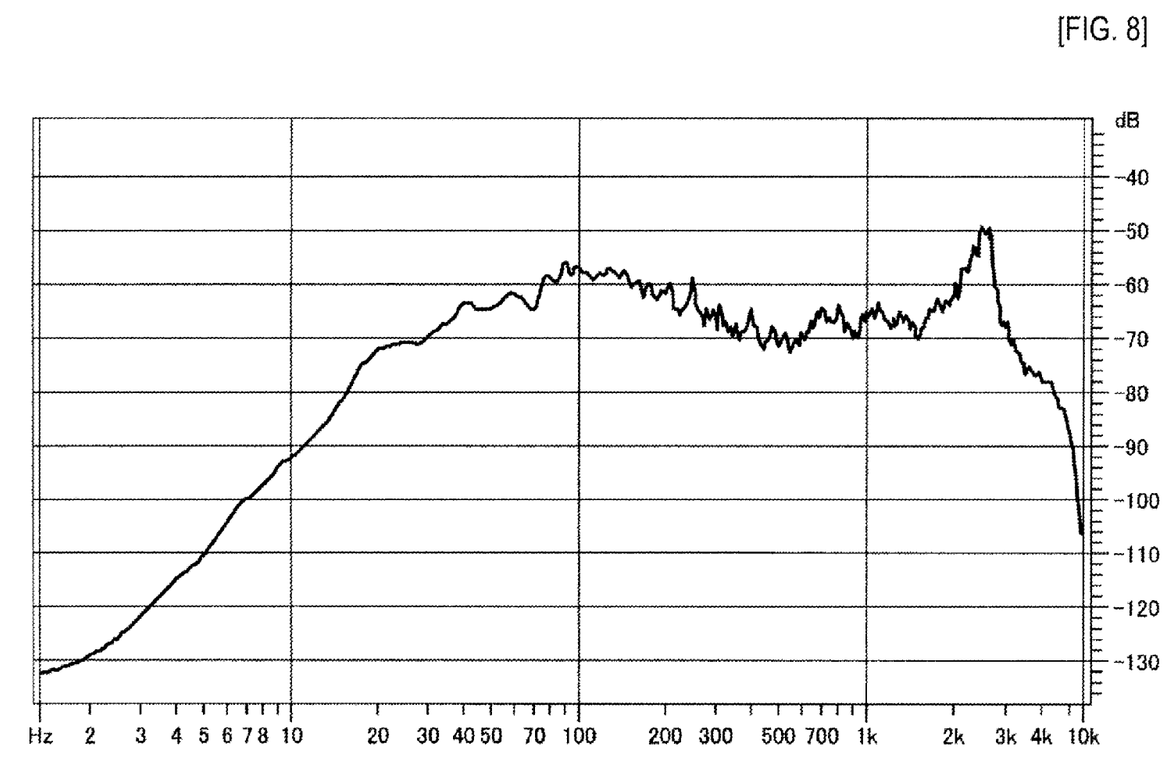
FIG. 8 is a diagram showing an example of a power spectrum obtained via a Fourier transform of the sounds detected by the sound detecting element M1 of the biological sound measurement device 1 in a non-contact state.
Figure 9:
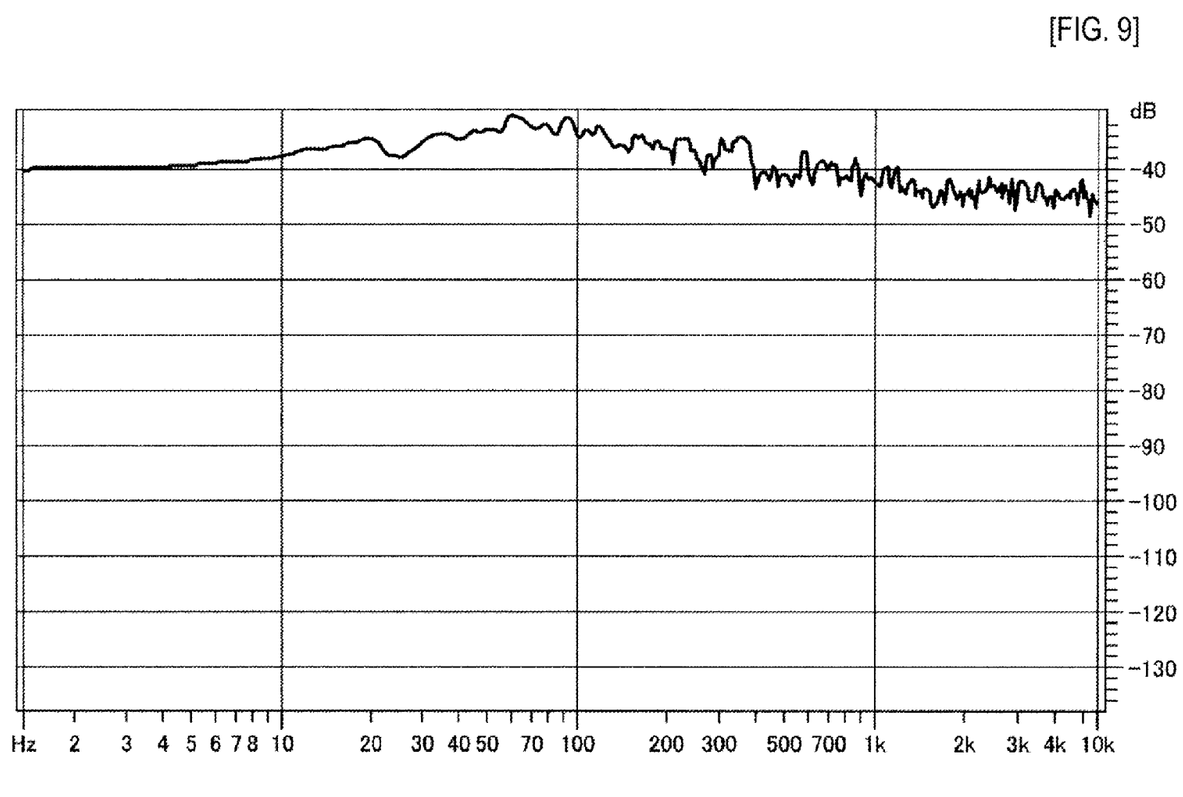
FIG. 9 is a diagram showing an example of a power spectrum obtained via a Fourier transform of the sounds detected by the sound detecting element M1 of the biological sound measurement device 1 in a contact state.

FIGS. 8 and 9 are diagrams showing examples of a power spectrum obtained via a Fourier transform of the sounds detected by the sound detecting element M1 of the biological sound measurement device 1. FIG. 8 shows measurement results of sounds when the measuring unit 3 is not in contact with the body surface S. FIG. 9 shows measurement results of sounds when the measuring unit 3 is in contact with the body surface S.

As can be seen in FIG. 9, when the measuring unit 3 is brought in contact with the body surface S, the power greatly increases, particularly in the 100 Hz and below frequency band of the detection frequency band (1 Hz to 10 kHz) of the sound detecting element M1. This is thought to be due to the housing space SP1 being sealed when a contact state is active and the sensitivity of the low frequency region increasing.

Based on this knowledge, the contact state determination unit 41 sets a frequency band of 100 Hz and below, for example, as the specific frequency band and calculates the square root of the mean (the RMS value) of the power in the specific frequency band of the sounds detected by the sound detecting element M1 as the sound pressure level. Then, the contact state determination unit 41 determines that a contact state is active in a case where a state of the RMS value being greater than a predetermined threshold continues for a certain amount of time.

As described above, according to the third modified example, only the sound pressure level of the specific frequency band is monitored when determining the contact state. As a result, it is possible to eliminate the effects of noise occurring in high frequency bands, and it is possible to increase the accuracy of determining the contact state. Note that the upper limit value of the specific frequency band may be determined taking into account the degree of sound pressure rising and noise elimination in the contact state, and may be 200 Hz, 90 Hz, 80 Hz, 70 Hz, or the like.

While various embodiments have been described with reference to the drawings, it goes without saying that the present invention is not limited to such examples. It will be appreciated by those skilled in the art that various modifications or revisions may be made within the scope of the claims, which are understood to naturally fall within the technical scope of the invention. Moreover, the components of the above-described embodiments may be optionally combined in a range that does not depart from the spirit of the invention.

The present application is based on Japanese Patent Application filed on Feb. 6, 2019 (Japanese Patent Application 2019-020130), the contents of which are incorporated herein by reference.

REFERENCE SIGNS LIST

1 Biological sound measurement device
1b Body portion
1a Head portion
2 Case
3 Measuring unit
3a Pressure receiving unit
4 Control unit
41 Contact state determination unit
42 Control unit
5 Battery
6 Display unit
S Body surface
Ha Hand
31 Housing
SP1 Housing space
32 Housing cover
M1 Sound detecting element

The invention claimed is:

1. A biological sound measurement device, comprising:
a sound collecting unit that detects biological sounds of a living body in a state of contact with a body surface of the living body; and
a contact state determination unit that determines whether or not a contact state is active in which the sound collecting unit is in contact with the body surface, based on a change in a sound pressure level of the biological sounds detected by the sound collecting unit, wherein
the contact state determination unit determines the contact state to be active in a case where, after the sound pressure level increases by a value equal to or greater than a first threshold, the sound pressure level decreases by a value equal to or greater than a second threshold and less than the first threshold.

2. The biological sound measurement device according to claim 1, wherein
the contact state determination unit determines whether or not the state is active in which the sound collecting unit is in contact with the body surface, based on a change in the sound pressure level of a specific frequency band of the biological sounds detected by the sound collecting unit.

3. The biological sound measurement device according to claim 2, wherein
the specific frequency band is a frequency band of 100 Hz and below.

4. The biological sound measurement device according to claim 1, further comprising a control unit that analyzes the biological sounds detected by the sound collecting unit and notifies of an analysis result, wherein
the control unit starts analysis of the biological sounds in a case where the contact state determination unit determines that the contact state is active.

5. The biological sound measurement device according to claim 4, wherein
the control unit analyzes the biological sounds and notifies of an analysis result of the analysis that was started indicating whether or not a wheeze is included in the biological sounds.

6. A biological sound measurement device, comprising:
a sound collecting unit that detects biological sounds of a living body in a state of contact with a body surface of the living body; and
a contact state determination unit that determines whether or not a contact state is active in which the sound collecting unit is in contact with the body surface, based on a change in a sound pressure level of the biological sounds detected by the sound collecting unit, wherein
the contact state determination unit determines the contact state to be active in a case where, after the sound pressure level increases by a value equal to or greater than a first threshold and then the sound pressure level decreases by a value equal to or greater than a second threshold and less than the first threshold, an amount of fluctuation in the sound pressure level is equal to or less than a third threshold continuously for a predetermined amount of time.

7. A biological sound measurement device, comprising:
a sound collecting unit that detects biological sounds of a living body in a state of contact with a body surface of the living body; and
a contact state determination unit that determines whether or not the contact state is active in which the sound collecting unit is in contact with the body surface, based on a change in a sound pressure level of the biological sounds detected by the sound collecting unit, wherein
the contact state determination unit determines the contact state to be active in a case where, after the sound pressure level increases by a value equal to or greater than a first threshold and then the sound pressure level decreases by a value equal to or greater than a second threshold and less than the first threshold, a biological sound is determined to be included in the biological sounds detected by the sound collecting unit.

8. A control method for a biological sound measurement device, comprising:
determining whether or not a contact state is active in which a sound collecting unit of the biological sound measurement device, the sound collecting unit detecting biological sounds of a living body in a state of contact with a body surface of the living body, is in contact with the body surface, based on a change in a sound pressure level of the biological sounds detected by the sound collecting unit, wherein
in the determining, the contact state is determined to be active in a case where, after the sound pressure level increases by a value equal to or greater than a first threshold, the sound pressure level decreases by a value equal to or greater than a second threshold and less than the first threshold.

* * * * *